(12) United States Patent
Velten et al.

(10) Patent No.: US 9,274,047 B2
(45) Date of Patent: Mar. 1, 2016

(54) METHODS AND APPARATUS FOR IMAGING OF OCCLUDED OBJECTS

(71) Applicants: Andreas Velten, Madison, WI (US); Ramesh Raskar, Cambridge, MA (US)

(72) Inventors: Andreas Velten, Madison, WI (US); Ramesh Raskar, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/287,811

(22) Filed: May 27, 2014

(65) Prior Publication Data

US 2014/0347676 A1  Nov. 27, 2014

Related U.S. Application Data

(60) Provisional application No. 61/827,332, filed on May 24, 2013, provisional application No. 61/827,591, filed on May 26, 2013.

(51) Int. Cl.

| | |
|---|---|
| G01B 11/14 | (2006.01) |
| G01N 21/27 | (2006.01) |
| G01B 11/25 | (2006.01) |
| G01N 21/25 | (2006.01) |
| G01N 21/64 | (2006.01) |
| G01J 3/02 | (2006.01) |
| G01J 3/10 | (2006.01) |
| G01J 3/42 | (2006.01) |
| G01N 21/31 | (2006.01) |

(52) U.S. Cl.
CPC ............ *G01N 21/27* (2013.01); *G01B 11/2513* (2013.01); *G01J 3/021* (2013.01); *G01J 3/027* (2013.01); *G01J 3/10* (2013.01); *G01J 3/42* (2013.01); *G01N 21/255* (2013.01); *G01N 21/6456* (2013.01); *G01N 2021/3129* (2013.01); *G01N 2021/6417* (2013.01)

(58) Field of Classification Search
CPC ........... G01B 11/2513; G01B 2210/52; G01B 27/017; G01B 1/002; G01B 1/11; G01B 1/113; G01B 2027/0178; G01B 2207/107; G01B 5/124; G01B 6/001; G01C 21/20; G01C 21/3407; G01C 21/3632; G01C 21/3638
See application file for complete search history.

(56) References Cited

U.S. PATENT DOCUMENTS

| | | | |
|---|---|---|---|
| 8,538,183 B1 * | 9/2013 | d'Eon et al. | 382/252 |
| 2004/0239673 A1 * | 12/2004 | Schmidt | 345/426 |
| 2012/0075423 A1 * | 3/2012 | Kirmani et al. | 348/46 |
| 2012/0300062 A1 | 11/2012 | Pandharkar et al. | |
| 2013/0100250 A1 | 4/2013 | Raskar et al. | |

OTHER PUBLICATIONS

Velten, A. (2012) Recovering three-dimensional shape around a corner using ultrafast time-of-flight imaging. Nature Communications 3, Article 745, Macmillan Publishers Ltd., Mar. 2012.

* cited by examiner

*Primary Examiner* — Michael P Stafira
(74) *Attorney, Agent, or Firm* — Stephen R. Otis

(57) ABSTRACT

An active imaging system, which includes a light source and light sensor, generates structured illumination. The light sensor captures transient light response data regarding reflections of light emitted by the light source. The transient light response data is wavelength-resolved. One or more processors process the transient light response data and data regarding the structured illumination to calculate a reflectance spectra map of an occluded surface. The processors also compute a 3D geometry of the occluded surface.

4 Claims, 5 Drawing Sheets

METHODS AND APPARATUS FOR IMAGING OF OCCLUDED OBJECTS

RELATED APPLICATIONS

This application is a non-provisional of, and claims the benefit of the filing date of, U.S. Provisional Application No. 61/827,332, filed May 24, 2013, and U.S. Provisional Application No. 61/827,591, filed May 26, 2013, the entire disclosures of which are herein incorporated by reference.

FIELD OF THE TECHNOLOGY

The present invention relates generally to imaging that captures a set of transient light response data. Such imaging is sometimes called time-of-flight imaging.

SUMMARY

In exemplary implementations of this invention, an active imaging system "looks around a corner" to determine spatially registered reflectance spectra of an occluded object. The occluded object is not in the direct line of sight of the imaging system, but is occluded behind an opaque object. The imaging system can "look around the corner" by using light reflecting from a visible surface, such as an ordinary, diffusely reflective wall.

The active imaging system, which includes a light source and light sensor, generates structured illumination. The light sensor captures transient light response data regarding reflections of light emitted by the light source. The transient light response data is wavelength-resolved. One or more processors process the transient light response data and data regarding the structured illumination to calculate a reflectance spectra map of an occluded surface. The processors also compute a 3D geometry of the occluded surface.

In exemplary implementations of this invention, the structured illumination varies as a function of (a) time, (b) wavelength, and (c) projection position or sensor position (or both). The structured illumination includes (a) three or more linearly independent projection patterns, (b) three or more linearly independent detection patterns, or (c) three or more linearly independent combinations, where each respective combination is a combination of a projection pattern or a detection pattern. In the preceding sentences: a) a projection position is a spatial position of a pixel on a projection surface; (b) a sensor position is a spatial position of a pixel of a light sensor; (c) a projection pattern is a pattern of intensity of projected light, which pattern varies as a function of projection position; and (d) a detection pattern is a pattern of detection intensity, which pattern varies as a function of sensor position. In the preceding sentence, detection intensity is either (a) intensity of light actually measured by the light sensor or (b) a calculated intensity computed by a computer as a function of light intensity actually measured by the light sensor.

A problem with imaging an occluded object using reflections off a diffusely reflective surface (such as an ordinary wall) is attenuation of light: very little of the light that initially leaves the light source gets back to the light sensor (after reflecting off the diffusely reflective surface, then off the occluded object, then off the diffusely reflective surface). This attenuation tends to reduce the spatial and frequency resolution of the imaging system.

To mitigate this attenuation, the radiant power of the light source may be increased. However, if the radiant power of the light source is increased too much, the light may burn the visible surface, damage a human user's eyes, or cause failures in the light source itself. For example, a powerful laser beam may burn a hole in a diffusely reflective wall. A bright laser may also be dangerous to the human eye and require additional safety measures to make the device eye-safe.

In some implementations of this invention, the light source directly illuminates only a single position on the visible surface at any given time. An advantage of this approach is that it can, in some cases, reduce computational load. A disadvantage of this approach, however, is that it exacerbates the light attenuation (and thus the reduction in resolution) discussed above, because it concentrates all of the light on a single position, and thus reduces the radiant power of the light source that can be safely used.

In some implementations of this invention, a light source directly illuminates a large area of a visible surface at a single time, rather than only a single position of the visible surface at a single time. An advantage of this "large area" approach is that the radiant power emitted by the light source can be greater, thus mitigating the attenuation problem discussed above.

The imaging system can detect useful spectral information about the occluded object. It can determine, for each respective 3D position in a set of positions on the surface of the occluded object, the spectral intensity of light reflecting from that position. This spectral information contains information about material properties of the occluded object, and thus can be used for classification of occluded objects. For example, the occluded object may be mammalian tissue, and the classification may be for diagnostic purposes. The imaging system can have a very high spectral resolution.

Also, the imaging system can determine the 3D geometry of a surface of the occluded object.

Here is a brief, non-limiting overview of how the imaging system works:

The imaging system includes an ultra-fast light sensor. For example, the light sensor may have a temporal resolution in the picosecond range. The light sensor is so fast (has sufficient temporal resolution) that it captures transient light responses to the illumination. That is, if the light source emits light at an initial time, the light sensor can distinguish between different reflections of that light that arrive at the light sensor at different times after the initial time, due to traveling in different paths with different path lengths. For example, if the light source emits light at time t=0, then the light sensor can distinguish between a reflection of that light which arrives at the sensor at t=X picoseconds and another reflection of that light that arrives at the sensor at t=y picoseconds, where x≠y. For example, reflected light that travels a single-bounce light path (from light source to visible surface to light sensor) may arrive earlier than light that travels a three-bounce light path (from light source to visible surface to occluded object to visible surface to light sensor).

Computations performed by the imaging system assume that, or at least are not inconsistent with the assumption that, the sensor measurements occur under conditions in which the system operates as a linear system.

The sensor data may be specific in time (when was a certain intensity emitted and when was it detected), space (at what point in the visible scene was the illumination light projected and at what point was it detected), and wavelength (what is the wavelength of the detected light). One way to achieve this specificity is to create a light source that illuminates only one point in the visible scene for only one short time interval (e.g. a picosecond) and at only one narrow wavelength range combined with a detector that can detect the time, point of origin in the visible scene and wavelength of the detected signals.

However, rather than use a set of impulses in space, time and wavelength, the imaging system may instead use any other set of patterns that form a basis such that any desired pattern may be represented as a linear combination of the patterns actually used. Here are some non-limiting examples:

Example A: (A Pattern in Space): A light source emits a temporal sequence of spatial light patterns (first a first light pattern, then a second light pattern, and so on) and a light sensor captures images of the scene illuminated by these different patterns (first a first image of the scene illuminated by the first light pattern, then a second image of the scene illuminated by the second light pattern, and so on). These images can be computationally combined in a linear combination to create any other possible spatial pattern on the wall down to a desired spatial resolution (i.e. they form a basis). Data collected for each of the patterns may be summed to create data corresponding to any possible spatial pattern from the data collected for one set of basis patterns. For example, a computer may calculate data that would have been collected for a series of point illuminations.

Example B (A Pattern in Time): A light source is modulated so that the light source emits light which forms a pattern in the temporal domain. The data for this temporal pattern is collected and another temporal pattern is projected. If the time patterns form a basis, one can compute the data that would be collected for any arbitrary time pattern from a linear combination of the collected data. For example, a computer may calculate the data that would have been collected for a short pulse. If the projected patterns are for example a set of sine functions with varying frequencies and phases, a computer may calculate a short pulse from these patterns by multiplying each of them with a real number and adding them. Applying the same linear combination to the collected data may yield the data for a short illumination pulse. For example, this linear combination may be achieved by modulating the gain of a slow detector, where the gain of the detector represents a temporal pattern that is multiplied to the collected data and the detector integrates collected light performing a summation.

In some cases, a first pattern may be a light pattern projected on a projection surface, and a second pattern may be a pattern of modulation of gain of a light sensor. The wavelength and phase of the first and second patterns, respectively, may be varied. Different combinations (of the wavelength and phase, respectively, of the first and second patterns, respectively) may be created.

Either the light source, light sensor or both may be wavelength-resolved. For example, a wavelength-resolved light source and a broadband light sensor may be used to gather data. Alternatively, a broadband light source and a wavelength-resolved light sensor may be used to gather data. Or both the light source and the light sensor may be wavelength-resolved.

In some implementations of this invention, the light source is both wavelength-resolved and wavelength-tunable. For example, the tunable, wavelength-resolved light source may comprise an optical parametric oscillator, optical parametric amplifier or tunable laser, such as a tunable Ti:sapphire laser.

In exemplary implementations, one or more processors execute a reconstruction algorithm that includes: (a) processing data indicative of light sensor data; (b) calculating a reflectance spectrum map and 3D spatial coordinates of each respective position out of a set of positions on a visible surface; and (c) calculating a reflectance spectrum map and 3D spatial coordinates of each respective position out of a set of positions on an occluded surface. Alternatively, all or part of the data in step (b) may be obtained from a map of the visual surface, which map is stored in electronic memory. In exemplary implementations, the one or more processors also perform an algorithm to mitigate noise, or enhance features, in a signal.

The description of the present invention in the Summary and Abstract sections hereof is just a summary. It is intended only to give a general introduction to some illustrative implementations of this invention. It does not describe all of the details of this invention. This invention may be implemented in many other ways. Likewise, the description of this invention in the Field of the Technology section is not limiting; instead it identifies, in a general, non-exclusive manner, a field of technology to which exemplary implementations of this invention generally relate.

Figure 1:
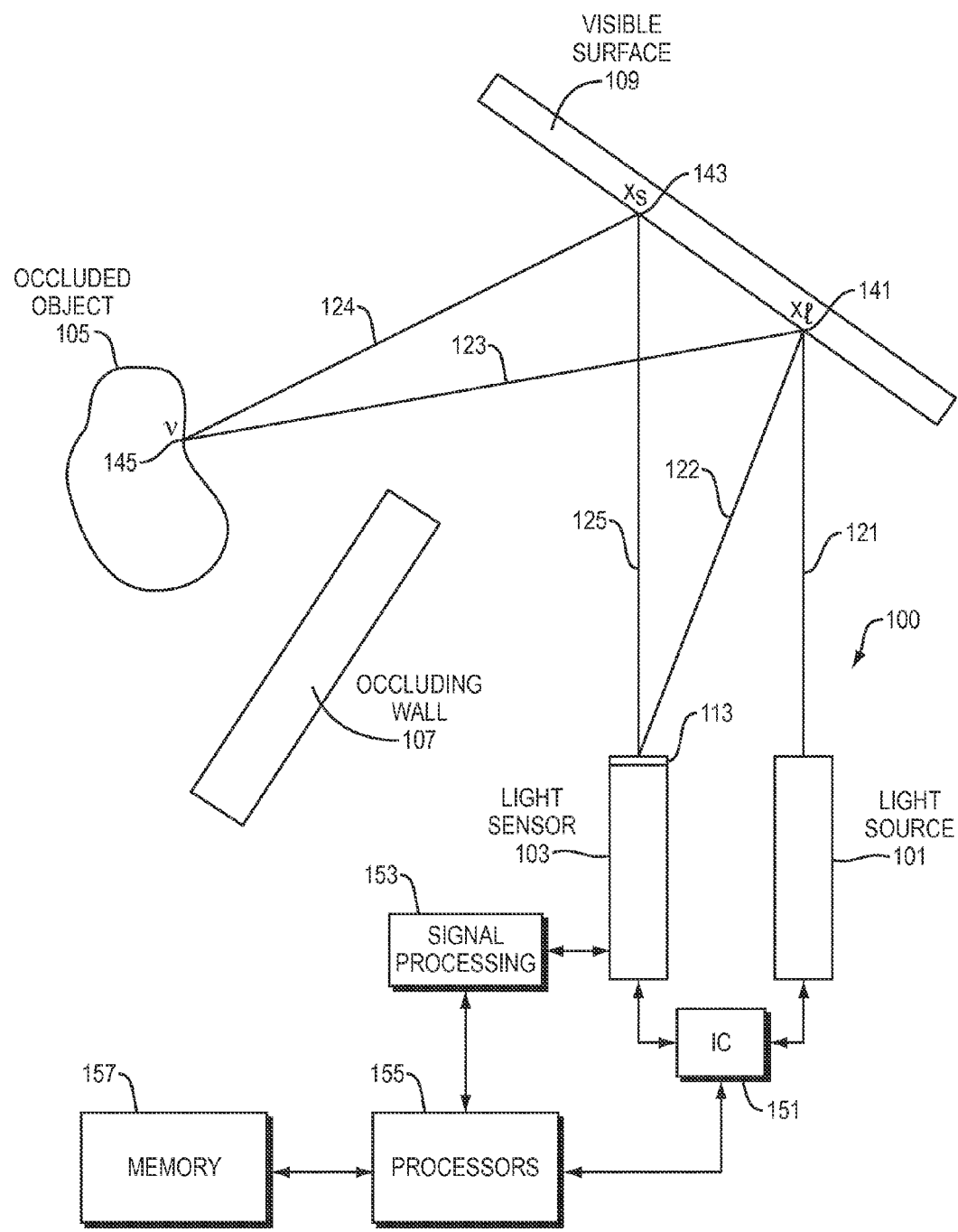
FIG. 1 shows an imaging system that can sequentially illuminate a set of positions on a visible surface, one position at a time.

The above Figures show some illustrative implementations of this invention, or provide information that relates to those implementations. However, this invention may be implemented in many other ways. The above Figures do not show all of the details of this invention.

DETAILED DESCRIPTION

In exemplary implementations of this invention, an imaging system uses a structured illumination to obtain spatially registered reflectance spectra from an occluded target. The occluded target is a surface or volume for which there is not a direct line of sight between the imaging system and the target.

A light source illuminates a visible surface. The visible surface can be seen directly from the light source and directly from the light sensor of the imaging system.

A portion of the light undergoes only one reflection: it travels directly from the light source to the visible surface, and then reflects from the visible surface directly back to the imaging system where it is detected by a fast light sensor with a broad spectral bandwidth. For example, the light sensor may comprise a picosecond streak camera or an avalanche photodetector.

Another portion of the light reflects three times, first from the visible surface, then from an occluded surface, and then from the visible surface. The light sensor detects both the single-bounce light and the three-bounce light with picosecond time resolution.

Actual Detection Patterns and Synthetic Detection Patterns:

In exemplary implementations of this invention, the detection pattern that would result from any actual pattern of emitted light may be emulated by a synthetic pattern: For example, an actual pattern of emitted light that varies over time, space or wavelength (or over any combination of two or more of time, space and wavelength) may be emulated by a synthetic pattern. The synthetic pattern may be created by a linear superposition of linearly independent patterns.

Actual Wavelength Band Detection Pattern: As used herein, "actual wavelength band detection pattern" means a light intensity pattern detected by a single pixel of a light sensor in response to actual emission of light in only a specific wavelength band.

Synthetic Wavelength Band Detection Pattern: In some implementations of this invention, the effect of emitting light in only a specific wavelength band can be emulated, even though light is not emitted only in that wavelength band. A synthetic wavelength band detection pattern can be obtained. As used herein, a "synthetic wavelength band detection pattern" means a light intensity pattern for a single pixel of a light sensor which is not the result of actual emission of light in only a specific wavelength band, but which is the same as would be detected by the single pixel in response to actual emission of light in only the specific wavelength band.

For example, a synthetic wavelength band detection pattern may be created as follows: A light source emits broadband light, and a first detection pattern is detected by the light sensor. Then the light source emits the broadband light, but filters out a specific wavelength band, and a second detection pattern is detected by the light sensor. The second detection pattern is subtracted from the first detection pattern. The resulting difference is equal to the detection pattern that would have been detected if only the specific wavelength band had been emitted.

More generally, a linear superposition of linearly independent patterns may be used to create a synthetic wavelength band detection pattern.

In illustrative implementations of this invention, wherever an actual wavelength band detection pattern occurs, a synthetic wavelength band detection pattern can be obtained instead. Thus, an apparatus that actually emits in only a narrow wavelength band is not required.

Actual Spatial Detection Pattern: As used herein, "actual spatial detection pattern" means a pattern of light intensity detected by a single pixel of a light sensor in response to an actual spatial pattern of light emitted by a light source.

Synthetic Spatial Detection Pattern: In some implementations of this invention, the effect of a spatial pattern of emitted light can be emulated, even though the spatial pattern is not actually emitted by the light source. A synthetic spatial detection pattern can be obtained. As used herein, a "synthetic spatial detection pattern" means a pattern of light intensity for a single pixel of a light sensor which is not the result of a specific spatial pattern of emitted light, but which is the same as would be detected by the single pixel if the specific spatial pattern of emitted light did occur.

For example, a synthetic spatial detection pattern may be created as follows: A light source emits light that directly illuminates an entire region of a visible surface, and a first detection pattern is detected by the light sensor. Then the light source emits light that directly illuminates the entire region, except for a specific set of positions in the region, and a second detection pattern is detected by the light sensor. The second detection pattern is subtracted from the first detection pattern. The resulting difference is equal to the detection pattern that would have been detected if only the specific set of spatial positions had been illuminated.

More generally, a linear superposition of linearly independent patterns may be used to create a synthetic spatial detection pattern.

In illustrative implementations of this invention, wherever an actual spatial detection pattern occurs, a synthetic spatial detection pattern can be obtained instead. Thus, problems associated with illuminating only a single position, or a small set of positions, on the visible surface can be avoided.

Actual Temporal Detection Pattern: As used herein, "actual temporal detection pattern" means a pattern of light intensity over time detected by a single pixel of a light sensor in response to an actual temporal pattern of light emitted by a light source.

Synthetic Temporal Detection Pattern: In some implementations of this invention, the effect of a temporal pattern of emitted light can be emulated, even though the temporal pattern is not actually emitted by the light source. A synthetic temporal detection pattern can be obtained. As used herein, a "synthetic temporal detection pattern" means a pattern of light intensity over time for a single pixel of a light sensor which is not the result of a specific temporal pattern of emitted light, but which is the same as would be detected by the single pixel if the specific temporal pattern of emitted light did occur.

For example, consider an actual pulse of light. The pattern of light intensity over time detected by a single pixel of the light sensor in response to the pulse of light would be an actual temporal detection pattern. The same detection pattern that is created by the actual pulse can emulated by a synthetic temporal detection pattern. For example, the synthetic temporal detection pattern may be obtained by modulating both the power of the light emitted by the light source and the gain of the light sensor are modulated. In that case, the light source may emit light over a long period of time, but the phases and wavelengths of the illumination pattern and the detection modulation pattern may be such that the same pattern is detected by a single pixel in the light sensor over a specific interval of time as would be detected the single pixel during the specific interval of time after an actual light pulse. For example, the phases and wavelengths of the illumination pattern and detection modulation pattern may be chosen such that the convolution of the two patterns equals zero at all times other than during the specific interval of time.

More generally, a linear superposition of linearly independent patterns may be used to create a synthetic temporal detection pattern.

In illustrative implementations of this invention, wherever an actual temporal detection pattern is detected, a synthetic pulse detection pattern can be obtained instead. Thus, actual light pulses do not need to be used.

Non-Infinitesimal Positions in Wavelength, Space or Time:

References herein to a single point in space, time or wavelength (e.g. to a spatial point, an instant in time or a single wavelength) shall be construed so as to avoid a trivial result in which light intensity associated with a single point in wavelength, time or space is zero due to the infinitesimally small size of the point.

To the extent necessary to avoid such a result, references to single points in wavelength, time or space shall be construed as follows: (a) a spatial "point" or "position" means a spatial region that includes the spatial point or position and has a spatial extent (in each of the spatial dimensions of the region) of $\epsilon$ nanometers; (b) a specified wavelength means a wavelength band that includes the specified wavelength, such that the magnitude of the difference between the greatest and the least wavelength in the wavelength band is $\epsilon$ nanometers; and (c) a specified instant of time means an interval of time that includes the specified instant, such that the magnitude of the difference between the greatest and the least time in the interval is $\epsilon$ nanoseconds. In the previous sentence, "$\epsilon$" is a non-zero positive real number, where $\epsilon \ll 1$.

Sequential Positions Approach:

In some implementations of this invention, the light source emits pulses of light to sequentially illuminate single positions on the visible surface, one position at a time. An advantage of this "sequential positions" approach is, in some cases, a lower computational load.

FIG. 1 shows an imaging system that can sequentially illuminate a set of positions on a visible surface, one position at a time.

In the example shown in FIG. 1, an occluded object 105 cannot be directly seen from the position of an imaging system 100, because an occluding wall 107 blocks the view.

A light source 101 emits pulses of illumination. Each pulse travels to an illumination position $x_l$ (e.g., 141) on a visible surface 109, and then reflects. A portion of the light in each pulse travels in a three-bounce light path $l \to x_l \to v \to x_s \to s$, where l is the light source, $x_l$ is the 3D position of an illumination position (e.g., 141) on visible surface 109, v is a voxel in the occluded space (e.g., 145), $x_s$ is the 3D position of a detection position (e.g., 143) on visible surface 109, and s is a pixel on the light sensor. For example, the path consisting of path segments 121, 123, 124, 125 is a three-bounce light path.

In the example shown in FIG. 1, another portion of the light in each pulse travels in a single-bounce light path $l \to x_l \to s$. For example, the path consisting of path segments 121 and 122 is a single-bounce light path.

In the example shown in FIG. 1, a series of measurements may be taken under different conditions as follows: The light source emits different wavelengths of light at different times: a first set of pulses at a first wavelength, then a second set of pulses at a second wavelength, and so on. For each wavelength, the light source emits a temporal sequence of pulses that illuminate different illumination positions on the visible surface at different times: first a first illumination position, then a second illumination position, and so on. The light sensor measures the transient response to each of the respective pulses for each of the respective wavelengths.

The result of this series of measurements is a set of eight dimensional data positions $I(x_l, x_s, t, \lambda)$ for each respective pixel in the light sensor, where I is the detected intensity, $x_l$ is the 3D position of an illumination position on the visible surface that is directly illuminated by the light source, $x_s$ is the 3D position of a detection position on the visible surface that is directly illuminated by reflected light from an occluded object and directly reflects light to the respective pixel, t is time at which light is detected, and $\lambda$ is the illumination wavelength. Thus, $I(x_l, x_s, t, \lambda)$ is the intensity detected at a given pixel at a given time, for a certain combination of illumination wavelength $\lambda$, illumination position $x_l$ and detection position $x_s$.

Note: $x_l$ and $x_s$ are each 3D spatial positions. However, if the visible surface is planar and the position and orientation of the visible surface are known, then $x_l$ and $x_s$ can each be specified by two spatial coordinates: e.g., x, y coordinates in the plane of the visible surface.

In the example shown in FIG. 1, an integrated circuit 151 sends control signals to control a light source 101 and a light sensor 103. For example, the integrated circuit 151 may comprise a microcontroller or field programmable gate array.

The light source 101 is tunable in that the wavelength of light emitted by the light source 101 may be varied over time.

For example, tunable light source 101 may comprise an optical parametric oscillator (OPO), optical parametric amplifier, or a tunable laser such as a tunable Ti:sapphire laser. Or, for example, the tunable light source 101 may comprise a single laser with a fixed emission wavelength, from which a set of wavelengths is created by nonlinear wavelength conversion. Or, for example, the tunable light source 101 may comprise an OPO and the wavelength of light emitted by the OPO may be varied by changing either (i) the pump wavelength of the OPO, (ii) the temperature, orientation or quasi-phasematching period of an optical crystal in the OPO, or (iii) the optical path length of the resonator in the OPO.

Alternatively, the light source 101 may comprise a set of light sources, each of which emits light at a different fixed wavelength. The wavelength emitted by this set of light sources may be tunable, in that the light sources in the set may be turned on one at a time in order to vary the wavelength of light emitted.

The range of wavelengths included in the data set depends on the particular implementation. For example, if the light source is an OPO (optical parametric oscillator), then the range of wavelengths emitted by the light source may be the entire range of the OPO (e.g., from about 400 nanometers to 2 microns). Or, for example, the light emitted by the light source may be visible, near-infrared, mid-infrared, or ultraviolet light. Or, for example, if the material composition of the occluded object is known, then the light source may, in some cases, emit one or more wavelengths that correspond to particular absorption spectra for the material(s).

The light sensor 103 captures light reflected from a visible surface 109. The light sensor 103 has sufficient temporal resolution that it can capture a transient light response. For example, if the light source emits a pulse of light, the light sensor can detect and distinguish between different reflections of the light pulse that arrive at the light sensor at different times, due to traveling in different paths with different path lengths. The larger the scene, the slower the time resolution that is needed.

For example, the light sensor 103 may comprise any of the following types of camera or sensor: (a) gated intensified CCD camera; (b) fast image intensifier; (c) streak camera; (d) photonic mixer device; (e) fast photodiode; (f) avalanche photodiode (APD); (g) APD array; and (h) photo multiplier.

If the light sensor 103 is a streak camera, then, in some cases, the streak camera images multiple detection positions $x_s$ (e.g., 143) positioned along a single straight line. In these cases, the multiple illumination positions $x_l$ (e.g., 141) are not located on that line.

Optionally, a filter or wavelength separating optic 113 is placed over the light sensor, to control the wavelength of light which the light sensor 103 can capture. For example, if a filter is used, the filter may block all but a narrow band of wavelengths from reaching the light sensor. If a wavelength separating optic (such as a prism or grating) is used, the wavelength separating optic may cause different wavelengths of light to be captured by different pixels in the light sensor.

Signal processing apparatus 153 processes signals from the light sensor 103, and outputs digital signals to one or more computer processors 155. For example, the one or more processors 155 may be housed in a computer. Data may be stored in electronic memory 157. The one or more processors 155 may read data from, or write data to, electronic memory 157.

Large Area Approach:

In some implementations of this invention, a light source directly illuminates an entire visible surface (or a large area of the visible surface) at a single time, rather than only a single point of the visible surface at a single time.

This "large area approach" increases the spatial and spectral resolution of the imaging system by increasing the allowable radiant power of the light source. The resolution that can be achieved in a time-of-flight imaging system to look around corners is limited by the radiant power that is used to illuminate the scene. If all light is concentrated on a single spot on the visible surface at a single time, then increasing the radiant power may cause damage.

In the "large area approach", the imaging system may instead illuminate the entire visible surface (or a large area of the visible surface) with a short pulse light signal. By distributing the power over a large area, it is possible to dramatically increase the radiant power of the light source, while leaving the irradiance at the visible surface constant. This in turn improves the spectral and frequency resolution of the imaging system. Alternatively, the "large area method" can be used to decrease the irradiance at the visible surface while leaving radiant power of the light source and reconstruction quality constant, for example to provide eye safety.

Figure 2A:
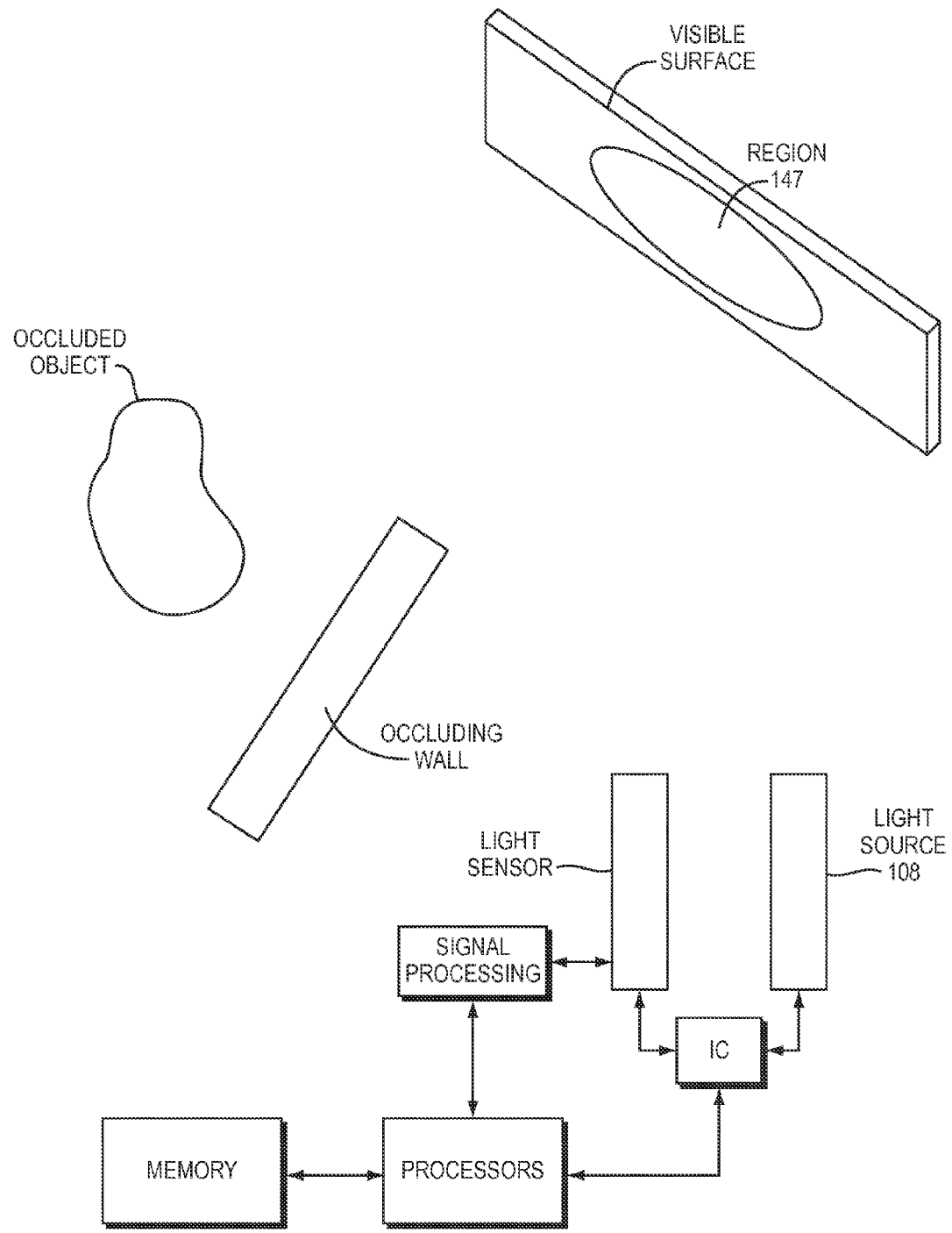
FIG. 2A shows an imaging system that can project a spatially varying light pattern onto multiple pixels of a visible surface at a single time.

FIG. 2A shows an active imaging system that can project a spatially varying light pattern onto multiple pixels of a visible surface at a single time. In the example shown in FIG. 2A, a light source 108 projects a spatially varying light pattern onto a large region 147 of a visible surface at a single time. The hardware of the active imaging system in FIG. 2A may be the same as in the hardware in FIG. 1, except in some cases the light source is different.

The light source used to project a spatially varying light pattern onto multiple pixels of a visible surface at a single time may vary, depending on the particular implementation of this invention.

Figure 2B:
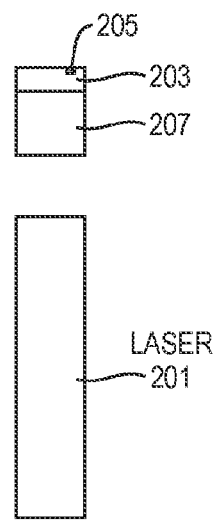
FIG. 2B shows a laser with a micromirror array, for use in projecting a spatially varying light pattern onto multiple pixels of a visible surface at a single time.

For example, FIG. 2B shows a wavelength-tunable laser 201 with a micro-mirror array 203, for use in projecting a spatially varying light pattern onto multiple pixels of a visible surface at a single time. Each pixel (e.g. pixel 205) in the micromirror array 203 comprises a MEMS (microelectromechanical system)—actuated mirror. The MEMS actuator for a single pixel can rotate or translate the MEMS-actuated mirror for the single pixel, so that in a first position, the mirror reflects laser light toward a region on the visible surface and that in a second position, the mirror reflects laser light toward a target that is not on the visible surface. For example, when the mirror is in the first position, the corresponding pixel on the visible surface is illuminated, and when the mirror is in the second position, the corresponding pixel on the visible surface is not illuminated. Optics 207 are used to split and guide light from the laser to the respective mirrors in the micromirror array. For example, the optics 207 may include a set of beam-splitters.

If the spatial pattern of light that is projected on the visible surface includes multiple illumination positions, then the recorded pattern is a linear superposition of patterns that would have been recorded for the constituent individual illumination positions. The illumination patterns may be chosen such that they form a basis in the space of possible collected data sets.

Figure 2C:
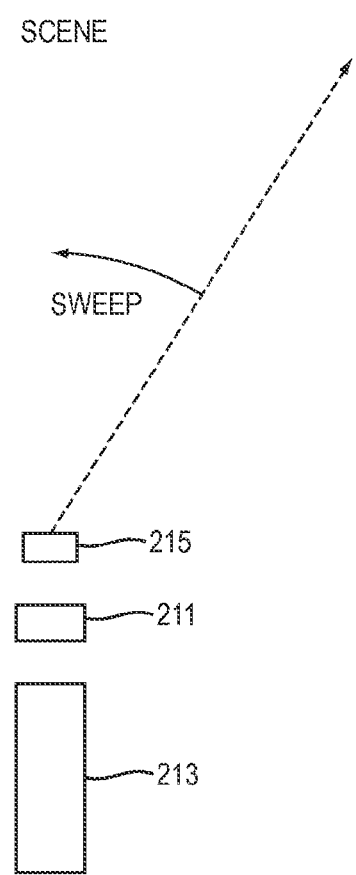
FIG. 2C shows a laser with a galvanometer-actuated mirror for sweeping a line of laser light across a scene.

Sweep:

In some implementations of this invention, a line of laser light is swept across a screen. FIG. 2C shows a wavelength-tunable laser with a galvo mirror for sweeping a line of laser light across a scene. A Powell lens 211 changes a point of laser light from a laser 213 into a line of laser light. A galvanometer-actuated mirror 215 rotates, causing the line of laser light to sweep across a visible surface. The light source, light sensor or both may be modulated during, or with respect to, the sweep. Projecting a line of laser light at any single time, rather than a point of laser light at a single time (as in the Sequential Positions Approach), mitigates the attenuation problem discussed above, although not as much as illuminating a wide area of the visible surface at a single time.

Special Cases:

In some implementations of this invention, the light source illuminates only a single spatial position at a time, or emits only a single very narrow wavelength band at a time, or emits light at only a single instant in time (i.e., emits a pulse).

However, these are all special cases of patterns that vary in intensity over space, wavelength or time.

For example, an illumination pattern that varies in intensity over multiple spatial positions may, in a special case, illuminate only one spatial position and leave the remaining spatial positions dark, which reduces to the special case of illuminating a single spatial position. Also, for example, an illumination pattern that varies in intensity over multiple wavelengths may, in a special case, consist of only a single very narrow wavelength band and have zero intensity for other wavelengths, which reduces to the special case of emitting only a single very narrow wavelength band. Also, for example, an illumination pattern that varies in intensity over time may, in a special case, have a non-zero intensity at only a single instant of time, which reduces to the special case of a light pulse.

In exemplary implementations of this invention, patterns vary in intensity over space, wavelength or time, and are not limited to these special cases. For example: (a) a light source may emit a specified set of multiple wavelength bands at a single time, and a response may be detected; or (b) a light source may emit different wavelength bands at different times, chosen such that the detected responses, when summed, are equal to the response that would be detected to the specified set of multiple wavelength bands. Or, for example (a) a light source may project light in specified spatial pattern that illuminates multiple positions on a visible surface at a single time, and a response may be detected; or (b) a light source may project light onto different spatial position(s) at different times, chosen such that the detected responses, when summed, are equal to the response to the that would be detected to the specified spatial pattern.

Figure 3:
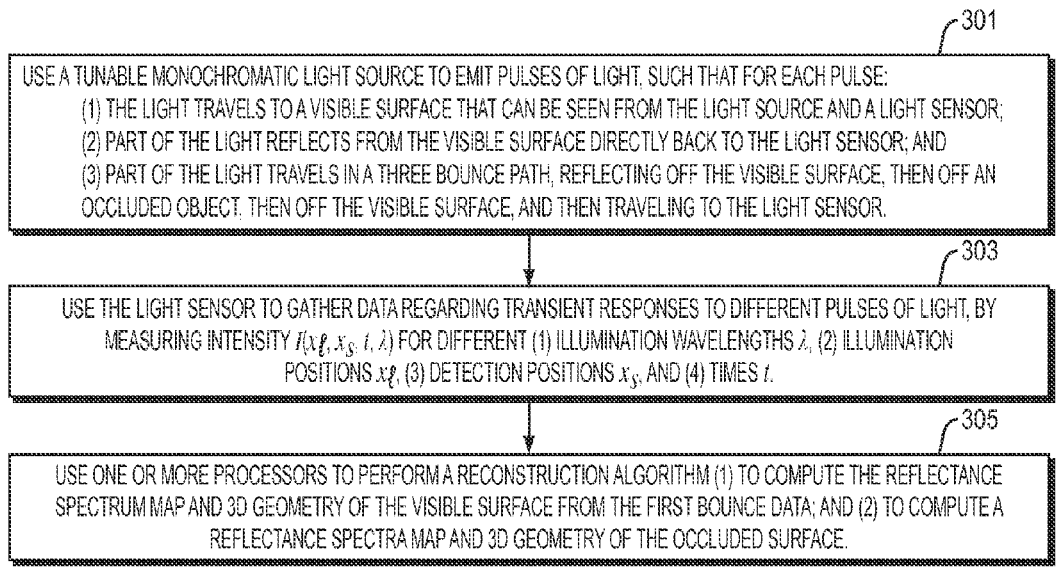
FIG. 3 shows steps in a method of spectroscopic imaging of an occluded object, using pulses of light.

Spectroscopic Imaging of an Occluded Object, Using Pulses of Light:

FIG. 3 shows steps in a method of spectroscopic imaging of an occluded object, using pulses of light. In the example shown in FIG. 3, the method includes the following three steps:

(1) Use a tunable monochromatic light source to emit pulses of light, such that for each pulse: (a) the light travels to a visible surface that can be seen from the light source and a light sensor, (b) part of the light reflects off the visible surface directly back to the light sensor, and (c) part of the light travels in a three-bounce path, reflecting off the visible surface, then off an occluded object, then off the visible surface, and then traveling to the light sensor. 301

(2) Use the light sensor to gather data regarding transient responses to different pulses of light, by measuring intensity $I(x_i, x_s, t, \lambda)$ of incident light at each respective pixel of the light sensor for different (a) illumination wavelengths $\lambda$, (b) illumination positions $x_i$, (c) detection positions $x_s$ and (d) times t. 303

(3) Use one or more processors to perform a reconstruction algorithm (a) to compute a reflectance spectrum map and 3D position of the first surface from the first bounce data, and (c) to compute a reflectance spectrum map and 3D spatial coordinates of each respective point, out of a set of points on the occluded surface. 305

In the algorithm shown in FIG. 3, for each respective pulse of light, time t specifies time elapsed after that pulse. For example, a reflection of a given pulse may arrive at the light sensor at time $t_1$ after the given pulse, and another reflection of the given pulse (which travels a longer light path with more "bounces") may arrive at the light sensor at a later time $t_2$ after the given pulse. In the algorithm shown in FIG. 3, time t is reset to 0 when a pulse occurs.

Reconstruction Algorithm:

In exemplary implementations of this invention, a variety of different reconstruction algorithms may be used to reconstruct, from the light sensor data, a spectral reflection map and 3D spatial geometry of an occluded surface. In these algorithms, the one or more processors assign a reflectance value to each voxel in the occluded volume for each illumination wavelength λ, out of a set of illumination wavelengths. Thus, the one or more processors calculate a spectrum for each respective position, out of a set of positions in the occluded space. The spectral resolution of this method may be a function of the spectral width and tunability of the light source and the bandwidth of the light sensor.

For example, one or more processors may execute a reconstruction algorithm that includes: (a) processing light sensor data captured at different illumination wavelengths; and (b) calculating a reflectance spectrum map of an occluded surface and estimating 3D spatial coordinates of each respective point, out of a set of points on the occluded surface.

Or, for example, one or more processors may perform a reconstruction algorithm that includes the steps of (i) analyzing a set of light sensor data $I(x_l, x_s, t, \lambda)$ for each respective pixel of the light sensor; (ii) using first bounce data to determine a reflectance spectrum map of a visible surface, or reading stored data regarding this reflectance spectrum map; (iii) using first bounce data to determine 3D spatial coordinates of each respective point out of a set of points on the visible surface, or reading stored data regarding this 3D geometry; (iii) calculating a reflectance spectrum map of the occluded surface; and (iv) calculating 3D spatial coordinates of each respective point out of a set of points on the occluded surface.

Figure 4:
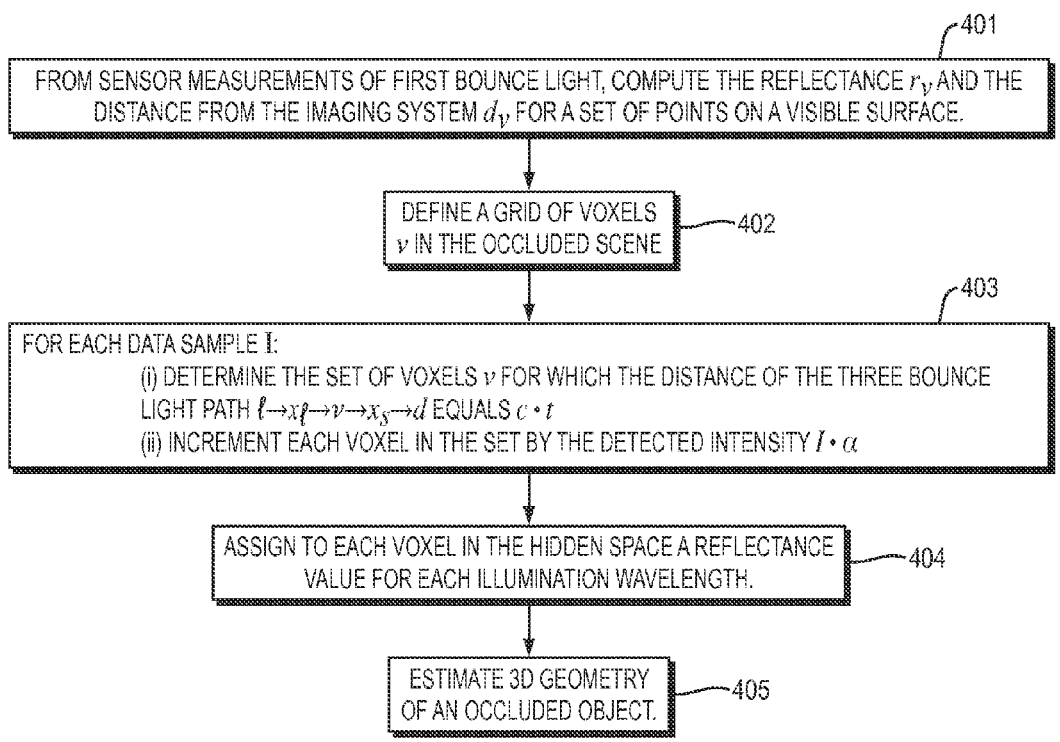
FIG. 4 shows steps in an example of a reconstruction algorithm.

FIG. 4 shows steps in an example of a reconstruction algorithm. This algorithm may be performed by one or more processors 155. In the example shown in FIG. 4, the reconstruction algorithm includes the following five steps:

(1) From sensor measurements of first bounce light, compute the reflectance $r_v$ and the distance from the imaging system $d_v$ for a set of positions on the visible surface. 401

(2) Define a grid of voxels v in the occluded scene 402, and initialize the intensity for each of the voxels v to zero.

(3) For each data sample I (a) determine the set of voxels v for which the distance of the three-bounce light path $l \rightarrow x_l \rightarrow v \rightarrow x_s \rightarrow s$ equals c·t, and (b) increment the intensity of each respective voxel in the set by an amount equal to I·α. 403

(4) Assign to each voxel in the occluded space a reflectance value for each illumination wavelength. 404

(5) Estimate a 3D position of an occluded object. 405

In the example shown in FIG. 4, all the voxels v that are located such that the distance of the three-bounce light path $l \rightarrow x_1 \rightarrow v \rightarrow x_s \rightarrow s$ equals c·t lie on the surface of an ellipsoid.

In the example shown in FIG. 4: I is detected intensity at a pixel of the light sensor; $x_l$ is the 3D spatial position of an illumination point on the visible surface that is directly illuminated by the light source; $x_s$ is the 3D spatial position of a detection point on the visible surface that is directly illuminated by reflected light from an occluded object and directly reflects light to the respective pixel; t is time at which light is detected; λ is illumination wavelength; c is the speed of light in a vacuum. Alternatively, c is a constant equal the product of the speed of light in a vacuum and a number, which number is greater than or equal to 0.9 and less than or equal to 1.0.

In the example shown in FIG. 4: (a) α is a constant (e.g., 1); or (b) α is a variable that represents what portion of light travels to a given voxel on the occluded surface (from a given illumination point on a visible surface) then reflects back to a given detection point on the visible surface and then reflects from there to the light sensor. If α is such a variable, then: (1) α is a function of, among other things, distance from the voxel to the detection point; and (2) some of the factors that affect α are initially known and others (such as albedo at the voxel) are not known. In some cases, if α is such a variable, then α is determined iteratively.

In the examples shown in FIGS. 3 and 4, if all illumination points are illuminated simultaneously, then the reconstruction algorithm performed by one or more processors may be modified as follows: Assume that the illumination came entirely from a first illumination point, and increment voxels accordingly, then assume that the illumination came entirely from a second illumination point, and increment voxels accordingly, and so on, for a certain number of illumination points. (The more illumination points, the better the image).

Figure 5:
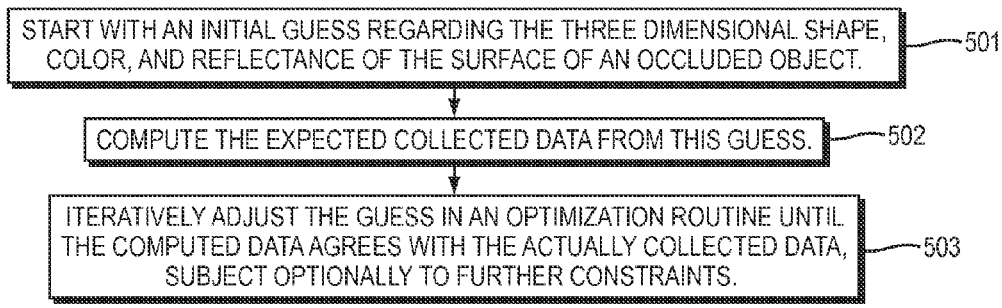
FIG. 5 shows steps in another example of a reconstruction algorithm.

FIG. 5 shows steps in another example of a reconstruction algorithm. Start with an initial guess regarding the three dimensional shape, color, and reflectance of the surface of the occluded object 501. Compute the expected collected data from this guess 502. Iteratively adjust the guess in an optimization routine until the computed data agrees with the actually collected data, subject optionally to further constraints 503. For example, the further constraints may include limiting the reconstructed data to a depth map, rather than a complete three dimensional volume.

Enhancement Algorithm:

The one or more processors may also perform an enhancement algorithm that reduces noise in a signal or otherwise enhances features in the signal.

For example, the enhancement algorithm may include the step of taking a second derivative of the reconstructed voxel space, the second derivative being taken along the normal of the visible surface. Or, for example, the enhancement algorithm may include the step of taking a Laplacian $$V_{enhanced}(x, y, z) = \frac{\partial^2 V}{\partial x^2} + \frac{\partial^2 V}{\partial y^2} + \frac{\partial^2 V}{\partial z^2}$$

where x, y, and z are the 3D spatial coordinates of a voxel, V is the computed accumulated intensity of a voxel (e.g., from part (b) of step 403 of the algorithm shown in FIG. 4), and $V_{enhanced}(x,y,z)$ is the accumulated intensity for a voxel with an improved contrast for discrete surfaces in the occluded object.

Other enhancement algorithms may be used instead of, or in addition to, the enhancement algorithms described above. For example, the results of the reconstruction algorithm may be improved by: (a) a filtered backprojection with an appropriate filter, such as a Hann (also known as Hanning) filter; (b) a Hough transform; (c) a classification algorithm (e.g., nearest neighbor or support vector machine) that detects features in the data based on computed or measured data of expected object shapes and spectra; or (d) a machine learning method, such as a neural network or a genetic algorithm to learn how to match object shapes and spectra to collected datasets.

Structured Illumination:

In exemplary implementations of this invention, an active imaging system generates structured illumination.

A wide variety of modulated patterns can be used to produce structured illumination. For example, structured illumination may include a random intensity sequence or a set of sinusoidal or periodic patterns. For example, the light source can project an illumination pattern, and a detection modulation pattern can be applied to vary gain of the light sensor, such that both patterns are sinusoidal or periodic. The relative phases and wavelengths of these two patterns may be varied, to create a set of different patterns. Or, for example, the light source can project a set of complex spatial patterns on the wall rather than a set of single illumination positions.

A light source, a light sensor, or both, may be modulated to generate structured illumination. For example, structured illumination may be generated by using one or more of the following modulation techniques:

Modulation of a light source in time may be achieved by modulating the power supply of the light source, by attenuating it with a fast shutter such as an electro-optical or acousto-optical modulator, by mode-locking it to create short pulses or modulations on a continuous laser output, or by creating a random laser with fast random intensity fluctuations.

A light sensor may be modulated by altering the analog gain of the detector as is done in a dynode modulated photomultiplier, by diverting the created signal from the detection circuitry as is done in a CMOS photonic mixer device, by adding a fast shutter such as an electro-optical or acousto-optical modulator, or by capturing the complete signal with sufficient time resolution and multiplying it with a modulation function.

Modulation in space may be achieved by modulating the light source with a digital micromirror device (DMD) and projecting that modulated pattern into the visible scene. This is done in digital video projectors. Alternatively the modulation may be achieved by using a matrix of liquid crystals as used in an LCD display. A spatial pattern may be achieved by scanning. For example, galvanometer-actuated mirrors may be used for scanning, and beam intensity may be modulated during the scan.

To modulate a light source in wavelength, a tunable laser or parametric oscillator may be used. Or, spectral intensity of a continuous (white) light source may be modulated, for example by separating different wavelengths with a grating or prism and then modulating the signal spatially by using one of the methods described above. After spatial modulation, the signal may be spatially recombined using a second grating or prism. Or, a light source may emit light with random spectral modulations and the resulting spectra may be measured.

Figure 6:
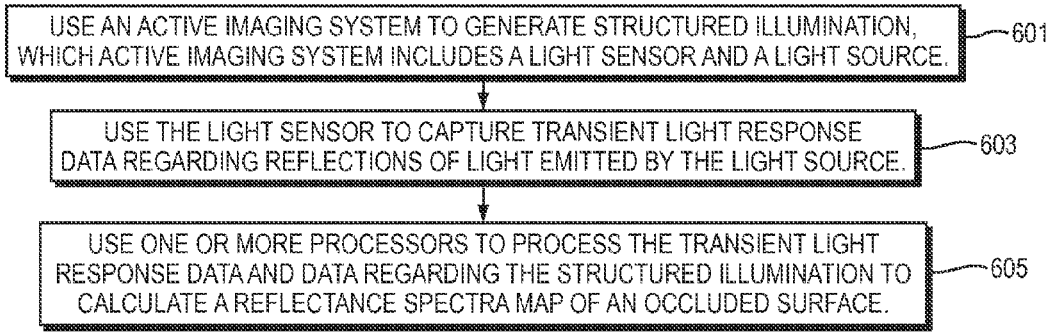
FIG. 6 shows steps in a method of imaging an occluded surface, using structured illumination.

FIG. 6 shows steps in a method of imaging an occluded surface, using structured illumination. In the example shown in FIG. 6, the method includes the following steps: Use an active imaging system to generate structured illumination, which active imaging system includes a light sensor and a light source 601. Use the light sensor to capture transient light response data regarding reflections of light emitted by the light source 603. Use one or more processors to process the transient light response data and data regarding the structured illumination to calculate a reflectance spectra map of an occluded surface 605.

Figure 7:
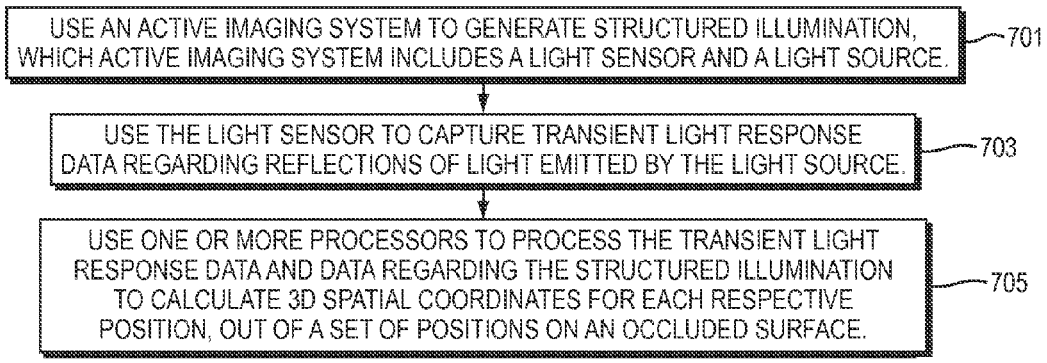
FIG. 7 shows steps in another method of imaging an occluded surface, using structured illumination.

FIG. 7 shows steps in another method of imaging an occluded surface, using structured illumination. In the example shown in FIG. 7, the method includes the following steps: Use an active imaging system to generate structured illumination, which active imaging system includes a light sensor and a light source 701. Use the light sensor to capture transient light response data regarding reflections of light emitted by the light source 703. Use one or more processors to process the transient light response data and data regarding the structured illumination to calculate 3D spatial coordinates for each respective position, out of a set of positions on an occluded surface 705.

Processors:

In exemplary implementations of this invention, one or more electronic processors are specially adapted: (1) to generate control signals to control hardware components of an imaging system (including a light source and light sensor), including modulate a light source or light sensor, to control wavelength, timing or direction of light emitted by one or more light sources, to tune the wavelength of light emitted by a light source, to turn different light sources on and off, to control a mirror galvanometer to raster a light beam, to control timing of light pulses, or to tune the wavelength of light detectable by a light sensor; (2) to calculate, or read from memory, reflectance values or position of a visible surface; (3) to calculate, or read from memory, reflectance values or position of an occluded surface; (4) to perform a reconstruction algorithm; (5) to perform an algorithm to enhance signal features or reduce noise in a signal; (7) to calculate patterns for structured illumination; (8) to compute a linear superposition or basis transformation; (9) to receive signals indicative of human input, (11) to output signals for controlling transducers for outputting information in human perceivable format, and (10) to process data, to perform computations, to execute any algorithm or software, and to control the read or write of data to and from memory devices. The one or more processors may be located in any position or position within or outside of any housing for the light sensor or light source. For example: (a) at least some of the one or more processors may be embedded within or housed together with other components of the light source or light sensor, and (b) at least some of the one or more processors may be remote from the light source or light sensor The one or more processors may be connected to each other or to other components in the imaging system either: (a) wirelessly, (b) by wired connection, or (c) by a combination of wired and wireless connections. For example, one or more electronic processors (e.g., 155 in FIG. 1) may be housed in a computer, microcontroller, or field programmable gate array. Also, for example, one or more electronic processors may be housed in an integrated circuit (e.g., 151 in FIG. 1).

Alternative Implementations:

This invention is not limited to the implementations described above. Here are some non-limiting examples of other ways in which this invention may be implemented.

First bounce data: Alternatively, the first bounce data can be obtained in a separate step, by a different imaging system. Or, one or more processors may determine the first bounce data from a three dimensional map of the occluded volume that is stored in electronic memory 157.

Wavelength resolution in illumination and detection: In some cases, both the light source and light sensor are wavelength-resolved. For example, the light source may emit light at only a first set of wavelengths, and the light sensor may detect light at only a second set of wavelengths. In some implementations, the first and second sets of wavelengths overlap. In other implementations, the first and second sets of wavelengths do not overlap.

Fluorescence: In some implementations, an imaging system that has a wavelength-resolved illumination source and a wavelength-resolved light sensor can detect fluorescent materials, which absorb at a certain wavelength and emit at another. (For example, fluorescent materials are added to most laundry detergents to enhance colors in clothing; they can therefore aid the identification of a human in the occluded space.)

Fluorescence is not produced simultaneously with the illumination pulse. The illumination is absorbed and fluorescence light is emitted over time with a certain material dependent half-life between few picoseconds and several microseconds. For long fluorescence lifetimes, this time delay may, unless mitigated, degrade the time resolution and sensitivity of the system. However, if the fluorescence lifetime and the fluorescence emission wavelength are known, then this problem may be mitigated by time-shifting time t for the fluorescent emission wavelength in the above reconstruction algorithm.

Known occluded object position: If the position of the occluded object is known, this position knowledge can be incorporated in the reconstruction algorithm, improving the spectral and reflectance data. In some cases, this position knowledge can also be used to detect angular dependence of reflectance.

In some, but not all, implementations of this invention, the structured illumination comprises a structured light code. For example, the light source may project time-multiplexed structured light codes, including (1) binary codes (with two primitives), (2) n-ary codes (with n primitives, where n>2), (3) Gray codes combined with phase-shifting or line shifting, or (4) hybrid codes (which use time-multiplexing and also take into account spatial neighborhood information).

EXAMPLE

Here is a description of an illustrative implementation of this invention, in which light from a light source travels to a light sensor in either a single-bounce light path or a three-bounce light path:

Consider a function S that relates a projected light pattern $P(x_p, \lambda_p, t_p)$ to a set of collected intensities $I(x_d, \lambda_d, t_d)$, where $x_p$ is the position of an illuminated point in the visible scene, $\lambda_p$ is the wavelength of the illuminating light, $t_p$ is the time of illumination, $x_d$ is the position on a surface in the visible scene where the intensity was collected, $\lambda_d$ is the wavelength of the detected illumination, and $t_d$ is the time at which the intensity was collected. Thus, $I=S(P)$.

The function S incorporates the geometry of the visible scene, the hidden object, and the capture system as well as other properties of the capture system such as an apparatus function limiting the system resolution.

In this illustrative implementation, a light source projects different patterns $P_n$ and a light sensor detects their corresponding intensity distributions $I_n$.

Because S is linear, linear combinations of P can be created to produce linear combinations of I computationally:

$$S(P_1)=I_1 \text{ and } S(P_2)=I_2 \rightarrow S(P_1+P_2)=I_1+I_2$$

and $$S(rP)=rS(P)=rI$$

where r is a scalar.

If data $I_n$ is collected for a set of $P_n$, where $P_n$ (n=1, 2, 3, ..., N) forms a basis for the data space (e.g., patterns with any time, frequency and space resolution in the scene and spectral region of interest), then processors can compute any other pattern $P_x$ as a linear combination of $P_n$ $$P_x = r_1 P_1 + r_2 P_2 + \ldots + r_N P_N$$

for the appropriate choice of $r_n$.

Because of the linearity of S, processors can then compute the dataset $I_x$ by simply applying the same linear combination to the data:

$$I_x = r_1 I_1 + r_2 I_2 + \ldots + r_N I_N$$

A special case, in which $P(x, \lambda, t)$ uses pulses in time, points in space, and narrowband lines in wavelength, represents one specific set of illumination conditions P that may form a basis. By the method described here this basis can be transformed to any other basis. Data can also be collected in a different basis, such as spatial patterns projected into the scene or time modulated signals rather than pulses. The linear combination technique described above can then be used to compute the data for pulsed illumination of individual points. Thus, the reconstruction algorithm that is described in FIG. 4 can be applied to any basis set of patterns in the measurement space.

DEFINITIONS

The terms "a" and "an", when modifying a noun, do not imply that only one of the noun exists.

An "active imaging system" means a system that includes a light source, a light sensor, and one or more computer processors.

The term "actual spatial detection pattern" is defined above.

The term "actual wavelength detection pattern" is defined above.

The term "actual temporal detection pattern" is defined above.

The term "comprise" (and grammatical variations thereof) shall be construed broadly, as if followed by "without limitation". If A comprises B, then A includes B and may include other things.

"Defined Term" means a term that is set forth in quotation marks in this Definitions section.

"Detection position" means (in the context of a system or apparatus that includes a light source and a light sensor, or in the context of a method that includes using a light source and a light sensor) a position on a surface, which position is illuminated by light that reflects directly from an occluded object to the position, and from which position light reflects directly to the light sensor.

The term "e.g." means for example.

The fact that an "example" or multiple examples of something are given does not imply that they are the only instances of that thing. An example (or a group of examples) is merely a non-exhaustive and non-limiting illustration.

Unless the context clearly indicates otherwise: (1) a phrase that includes "a first" thing and "a second" thing does not imply an order of the two things (or that there are only two of the things); and (2) such a phrase is simply a way of identifying the two things, respectively, so that they each can be referred to later with specificity (e.g., by referring to "the first" thing and "the second" thing later). For example, unless the context clearly indicates otherwise, if an equation has a first term and a second term, then the equation may (or may not) have more than two terms, and the first term may occur before or after the second term in the equation. A phrase that includes "a third" thing, a "fourth" thing and so on shall be construed in like manner.

"First bounce data" means data regarding single-bounce light.

The term "for instance" means for example.

"Herein" means in this document, including text, specification, claims, abstract, and drawings.

The terms "horizontal" and "vertical" shall be construed broadly. For example, "horizontal" and "vertical" may refer to two arbitrarily chosen coordinate axes in a Euclidian two dimensional space, regardless of whether the "vertical" axis is aligned with the orientation of the local gravitational field. For example, a "vertical" axis may oriented along a local surface normal of a physical object, regardless of the orientation of the local gravitational field.

"Illumination position" means (in the context of a system or apparatus that includes a light source, or in the context of a method that includes using a light source) a position on a surface, which position is illuminated by light that travels directly from the light source to the position.

The term "include" (and grammatical variations thereof) shall be construed broadly, as if followed by "without limitation".

"Intensity" means any measure of or related to intensity, energy or power. For example, the "intensity" of light includes any of the following measures: irradiance, spectral irradiance, radiant energy, radiant flux, spectral power, radiant intensity, spectral intensity, radiance, spectral radiance, radiant exitance, radiant emittance, spectral radiant exitance, spectral radiant emittance, radiosity, radiant exposure, radiant energy density and number of photons.

The term "light" means electromagnetic radiation of any wavelength. For example, "light" includes, among other things, visible light and infrared light. Likewise, any term that directly or indirectly relates to light (e.g., "imaging") shall be construed broadly as applying to electromagnetic radiation of any wavelength.

To say that a system is "linear" means that the system exhibits both the additivity property and scaling property. The additivity property means that, if a first cause has a first effect of the system and a second cause has a second effect on a system, then when both causes act on the system, the total effect will be the first effect plus the second effect. The scaling property means that for an arbitrary real or imaginary number k, if a cause is increased k-fold, then the effect is increased k-fold.

The term "magnitude" means absolute value.

The term "matrix" includes a matrix that has two or more rows, two or more columns, and at least one non-zero entry. The term "matrix" also includes a vector that has at least one non-zero entry and either (a) one row and two or more columns, or (b) one column and two or more rows. However, as used herein, (i) a scalar is not a "matrix", and (ii) a rectangular array of entries, all of which are zero (i.e., a so-called null matrix), is not a "matrix".

"Mid-infrared light" means light with a wavelength of between 2501 nm and 10 micrometers.

"Modulating" a light sensor means (i) modulating gain or a transfer function of the light sensor, or (ii) performing computations that emulate such modulating of the gain or the transfer function.

To "modulate" a light source means to modulate a light signal emitted by the light source.

To "multiply" includes to multiply by an inverse. Thus, to "multiply" includes to divide.

"Near-infrared light" means light with a wavelength of between 761 nm and 2500 nm.

"Occluded" means (in the context of a system or apparatus that includes a light sensor and a light source, or in the context of a method that includes using a light sensor and a light source) not directly visible from the position of the light sensor and not directly visible from the position of the light source.

The term "or" is inclusive, not exclusive. For example A or B is true if A is true, or B is true, or both A or B are true. Also, for example, a calculation of A or B means a calculation of A, or a calculation of B, or a calculation of A and B.

A parenthesis is simply to make text easier to read, by indicating a grouping of words. A parenthesis does not mean that the parenthetical material is optional or can be ignored.

The term "pixel" is not limited to a light sensor. For example, a light source may have pixels. Also, for example, a projection surface may have pixels. A "pixel" of a projection surface is the smallest addressable unit of the projection surface.

"Projection surface" means a surface onto which light is projected.

"Reflectance spectrum" means a set of data that maps a spectral intensity of reflected light to a particular wavelength or a particular waveband.

"Reflectance spectra map" means a set of data that specifies, for each respective spatial position out of a set of positions in a surface or volume, a reflectance spectrum of light reflecting from the respective spatial position.

To compute a term that "satisfies" an equation: (a) does not require that calculations involve terms, variables or operations that are in the equation itself, as long as the term itself (subject to error, as described in part (b) of this sentence) is computed; and (b) includes computing a solution that differs from a correct solution by an error amount, which error amount arises from one or more of (i) rounding, (ii) other computational imprecision, including error due to modeling a continuous signal by a discrete signal or due to using an insufficiently small step size in calculations, and (iii) signal noise or other physical limitations of sensors or other physical equipment.

As used herein, the term "set" does not include a so-called empty set (i.e., a set with no elements).

Mentioning a first set and a second set does not, in and of itself, create any implication regarding whether or not the first and second sets overlap (that is, intersect). For example, the phrase "transient light response data and data regarding the structured illumination" does not create any implication regarding whether or not the transient light response data and the data regarding the structured illumination overlap in any way.

"Single-bounce light" means light that travels a single-bounce light path.

"Single-bounce light path" means (in the context of a system or apparatus that includes a light sensor and a light source, or in the context of a method that includes using a light sensor and a light source) a path of light that starts at the light source and ends at the light sensor, during which path the light reflects only once.

"SI Projection Pattern" means a pattern of intensity of projected light, which pattern varies as a function of SI Projection Position.

"SI Projection Position" means spatial position of a pixel on a projection surface.

"SI Detection Pattern" means a pattern of intensity that varies as a function of SI Sensor Position, which intensity is either (a) an intensity of light actually measured by a light sensor or (b) an intensity of light computed by a computer as a function of light intensity actually measured by a light sensor.

"SI Pattern" means an SI Projection Pattern or SI Detection Pattern.

"SI Sensor Position" means spatial position of a pixel on a light sensor.

The term "structured illumination" means a set of SI Patterns, such that: (1) the set of SI Patterns varies as a function of (a) time, (b) wavelength, and (c) SI Projection Position or SI Sensor Position; and (2) the set of SI Patterns includes (a) three or more linearly independent SI Projection Patterns, (b) three or more linearly independent SI Detection Patterns, or (c) three or more linearly independent combinations, where each respective combination, out of the three or more linearly independent combinations, is a combination of an SI Projection Pattern and an SI Detection Pattern. "Data regarding structured illumination" includes data regarding the structured illumination itself or data regarding one or more direct or indirect effects of the structured illumination.

As used herein, a "subset" of a set consists of less than all of the elements of the set.

The term "such as" means for example.

The term "synthetic spatial detection pattern" is defined above.

The term "synthetic wavelength band detection pattern" is defined above.

The term "synthetic temporal detection pattern" is defined above.

"Third bounce data" means data regarding three-bounce light.

"3D" means three dimensional.

"Three-bounce light" means light that travels a three-bounce light path.

"Three-bounce light path" means (in the context of a system or apparatus that includes a light sensor and a light source, or in the context of a method that includes using a light sensor and a light source) a path of light that starts at the light source and ends at the light sensor, during which path the light reflects only three times, first from an illumination position, then from an occluded object, and then from a detection position.

"Transient light response data" means data that contains information about, and has sufficient temporal resolution to distinguish between, different reflections of light emitted by a light source at a single instant of time that arrive at a light sensor at different times.

"Ultra-violet light" means light with a wavelength of between 100 nm and 379 nm.

"Visible light" means light with a wavelength of between 380 nm and 760 nm.

"Visible surface" means (in the context of a system or apparatus that includes a light sensor and a light source, or in the context of a method that includes using a light sensor and a light source) a surface that is directly visible from the position of the light sensor and from the position of the light source.

Unless the context clearly requires otherwise, "wavelength" means wavelength of light.

A "wavelength-resolved" light sensor means a light sensor that maps each respective sensor reading, out of a set of sensor readings, to a particular wavelength out of a set of two or more wavelengths or to a particular waveband out of a set of two or more wavebands.

A "wavelength-resolved" light source means a light source configured to emit light while operating in a set of modes, such that light emitted in each respective mode, out of the set of modes, maps to a particular wavelength out of a set of two or more wavelengths or to a particular waveband out of a set of two or more wavebands.

To say that a set of data is "wavelength-resolved" means that each respective datum out of the set of data is mapped to a particular wavelength out of a set of two or more wavelengths or to a particular waveband out of a set of two or more wavebands.

To say that a light source is "wavelength-tunable" means that the wavelength(s) emitted by the light source may be adjusted. To say that a light source is "wavelength-tunable" means that the wavelength(s) captured or detected by the light source may be adjusted.

Spatially relative terms such as "under", "below", "above", "over", "upper", "lower", and the like, are used for ease of description to explain the positioning of one element relative to another. The terms are intended to encompass different orientations of an object in addition to different orientations than those depicted in the figures.

Except to the extent that the context clearly requires otherwise, if steps in a method are described herein, then: (1) steps in the method may occur in any order or sequence, even if the order or sequence is different than that described; (2) any step or steps in the method may occur more than once; (3) different steps, out of the steps in the method, may occur different number of times during the method, (4) any step or steps in the method may be done in parallel or serially; (5) any step or steps in the method may be performed iteratively; (5) a given step in the method may be applied to the same thing each time that the particular step occurs or may be applied to different things each time that the given step occurs; and (6) the steps described are not an exhaustive listing of all of the steps in the method, and the method may include other steps.

A matrix may be indicated by a bold capital letter (e.g., D). A vector may be indicated by a bold lower case letter (e.g., α). However, the absence of these indicators does not indicate that something is not a matrix or not a vector.

This Definitions section shall, in all cases, control over and override any other definition of the Defined Terms. For example, the definitions of Defined Terms set forth in this Definitions section override common usage or any external dictionary. If a given term is explicitly or implicitly defined in this document, then that definition shall be controlling, and shall override any definition of the given term arising from any source (e.g., a dictionary or common usage) that is external to this document. If this document provides clarification regarding the meaning of a particular term, then that clarification shall, to the extent applicable, override any definition of the given term arising from any source (e.g., a dictionary or common usage) that is external to this document. To the extent that any term or phrase is defined or clarified herein, such definition or clarification applies to any grammatical variation of such term or phrase, taking into account the difference in grammatical form. For example, grammatical variations include noun, verb, participle, adjective, or possessive forms, or different declensions, or different tenses. In each case described in this paragraph, Applicant is acting as Applicant's own lexicographer.

Variations:

This invention may be implemented in many different ways, in addition to those described above.

Here are some non-limiting examples of how this invention may be implemented:

This invention may be implemented as a method comprising, in combination: (a) using an active imaging system to generate structured illumination, which active imaging system includes a light sensor and a light source; (b) using the light sensor to capture transient light response data regarding reflections of light emitted by the light source; and (c) using one or more processors to process the transient light response data and data regarding the structured illumination to calculate a reflectance spectra map of an occluded surface. Furthermore: (1) the set of transient light response data may be wavelength-resolved; (2) the one or more processors may calculate three-dimensional spatial coordinates of each respective point in a set of points on the occluded surface; (3) the light source may be wavelength-resolved and wavelength-tunable; (4) the light source may emits a series of pulses of light, such that the light source emits a first wavelength during a first set of the pulses of light and not during other pulses in the series, the light source emits a second wavelength during a second set of the pulses of light and not during other pulses in the series, and the light source emits a third wavelength during a third set of the pulses of light and not during other pulses in the series, and the first, second and third sets of pulses of light do not overlap each other; (5) the light sensor may be wavelength-resolved and wavelength-tunable; (6) both the light sensor and the light source may be wavelength-resolved and wavelength-tunable; (7) the one or more processors may classify the occluded object based at least in part on the reflectance spectra map; (8) the occluded surface may comprise mammalian tissue; (9) the one or more processors may identify fluorescence that occurs in the occluded surface; (10) the one or more processors may identify a specific type of fluorescent material in the occluded surface, based at least on sensor data indicative of a specific absorption spectrum and specific emission spectrum of the occluded material; (11) the one or more processors may compute a reflectance spectra map for a visible surface; (12) the active imaging system may compute or detect a synthetic temporal detection pattern; (13) the active imaging system may compute or detect a synthetic wavelength band detection pattern; and (14) the active imaging system may compute or detect a synthetic spatial detection pattern. Furthermore, the one or more processors may perform an algorithm, which algorithm includes, for each data sample I (i) determining a set of voxels for which the distance of a three-bounce light path equals the product of c and t, and (ii) incrementing a calculated intensity of each respective voxel in the set of voxels by an amount equal to the product of I and $\alpha$, where: (a) each data sample I is a measured intensity at a single pixel of the light sensor for a particular illumination wavelength band, illumination position, detection position and time t; (b) c is a constant equal to the speed of light in a vacuum times a number, which number is greater than or equal to 0.9 and less than or equal to 1.0; and (c) $\alpha$ is (A) a constant or (B) a variable that is dependent on at least distance between the respective voxel and a detection position.

This invention may be implemented as a method comprising, in combination: (a) using an active imaging system to generate structured illumination, which active imaging system includes a light sensor and a light source; (b) using the light sensor to capture transient light response data regarding reflections of light emitted by the light source; and (c) using one or more processors to process the transient light response data and data regarding the structured illumination to calculate 3D spatial coordinates of each respective point, out of a set of points on an occluded surface. Furthermore, the one or more processors may compute a synthetic temporal detection pattern.

This invention may be implemented as an active imaging system comprising, in combination: (a) a light source for emitting light and a light sensor for capturing transient light response data regarding reflections of the light, which transient light response data is wavelength-resolved; and (b) one or more processors for processing the data to calculate a reflectance spectra map of an occluded surface. Furthermore, the active illumination system may be configured to generate structured illumination.

While exemplary implementations are disclosed, many other implementations will occur to one of ordinary skill in the art and are all within the scope of the invention. Each of the various embodiments described above may be combined with other described embodiments in order to provide multiple features. Furthermore, while the foregoing describes a number of separate embodiments of the apparatus and method of the present invention, what has been described herein is merely illustrative of the application of the principles of the present invention. Other arrangements, methods, modifications, and substitutions by one of ordinary skill in the art are therefore also within the scope of the present invention. Numerous modifications may be made by one of ordinary skill in the art without departing from the scope of the invention.

What is claimed is:

1. A method comprising, in combination:
   (a) using an active imaging system to generate structured illumination, which active imaging system includes a light sensor and a light source;
   (b) using the light sensor to capture transient light response data regarding reflections of light that is emitted by the light source and reflected from an occluded surface; and
   (c) using one or more processors to process the transient light response data and data regarding the structured illumination to calculate a reflectance spectra map of the occluded surface;
   wherein the light source is wavelength-resolved and wavelength-tunable.

2. A method comprising, in combination:
   (a) using an active imaging system to generate structured illumination, which active imaging system includes a light sensor and a light source;
   (b) using the light sensor to capture transient light response data regarding reflections of light that is emitted by the light source and reflected from an occluded surface; and
   (c) using one or more processors to process the transient light response data and data regarding the structured illumination to calculate a reflectance spectra map of the occluded surface;
   wherein the light source emits a series of pulses of light, such that:
      (i) the light source emits a first wavelength during a first set of the pulses of light and not during other pulses in the series;
      (ii) the light source emits a second wavelength during a second set of the pulses of light and not during other pulses in the series; and
      (iii) the light source emits a third wavelength during a third set of the pulses of light and not during other pulses in the series; and
      (iv) the first, second and third sets of pulses of light do not overlap each other.

3. A method comprising, in combination:
   (a) using an active imaging system to generate structured illumination, which active imaging system includes a light sensor and a light source;
   (b) using the light sensor to capture transient light response data regarding reflections of light that is emitted by the light source and reflected from an occluded surface; and
   (c) using one or more processors to process the transient light response data and data regarding the structured illumination to calculate a reflectance spectra map of the occluded surface;

wherein the light sensor is wavelength-resolved and wavelength-tunable.

4. A method comprising, in combination:
(a) using an active imaging system to generate structured illumination, which active imaging system includes a light sensor and a light source;
(b) using the light sensor to capture transient light response data regarding reflections of light that is emitted by the light source and reflected from an occluded surface; and
(c) using one or more processors to process the transient light response data and data regarding the structured illumination to calculate a reflectance spectra map of the occluded surface;
wherein:
(i) the light sensor is wavelength-resolved and wavelength-tunable; and
(ii) the light source is wavelength-resolved and wavelength-tunable.

* * * * *